US009524304B2

(12) United States Patent
Jayasundera et al.

(10) Patent No.: US 9,524,304 B2
(45) Date of Patent: Dec. 20, 2016

(54) SYSTEMS AND METHODS FOR DIAGNOSING INHERITED RETINAL DISEASES

(71) Applicant: THE REGENTS OF THE UNIVERSITY OF MICHIGAN, Ann Arbor, MI (US)

(72) Inventors: Kanishka T. Jayasundera, Ann Arbor, MI (US); Gail Hohner, Ann Arbor, MI (US); Jillian T. Huang, Ypsilanti, MI (US); Naheed W. Khan, Brownstown, MI (US); Matthew K. Johnson-Roberson, Chestnut Hill, MA (US); Daniel L. Albertus, Ann Arbor, MI (US); Ira Schachar, Ann Arbor, MI (US); Sarwar Zahid, Jamaica, NY (US); Amani Al-Tarouti, Ann Arbor, MI (US); Christopher R. Ranella, Macomb, MI (US); Zhao Huang, Ann Arbor, MI (US); Andrew M. Lynch, Oak Lawn, IL (US); Carla S. Kaspar, Davidson, MI (US); Nathan T. Patel, Ann Arbor, MI (US); Adnan Tahir, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 277 days.

(21) Appl. No.: 14/493,712

(22) Filed: Sep. 23, 2014

(65) Prior Publication Data
US 2015/0088870 A1 Mar. 26, 2015

Related U.S. Application Data

(60) Provisional application No. 61/881,711, filed on Sep. 24, 2013.

(51) Int. Cl.
*G06F 17/30* (2006.01)
*G06F 19/00* (2011.01)

(52) U.S. Cl.
CPC ..... *G06F 17/30256* (2013.01); *G06F 17/3053* (2013.01); *G06F 19/321* (2013.01); *G06F 19/345* (2013.01)

(58) Field of Classification Search
CPC ............ G06F 17/30256; G06F 17/3053; G06F 17/30244; G06F 17/30241; G06F 17/30091; G06F 17/301; G06F 19/345; G06F 19/321; G06F 19/3431; G06F 19/3437; G06F 19/3443; G06F 19/3487; G06F 19/36; G06K 9/62

(58) Field of Classification Search
USPC ............... 707/607, 737, 748, 755, 758, 765, 780,707/805, 941, 999.107; 600/300, 318, 600/356; 705/1.1, 2, 3
See application file for complete search history.

(56) References Cited

U.S. PATENT DOCUMENTS 5,692,220 A * 11/1997 Diamond ......... G01N 35/00603
600/368
5,868,134 A * 2/1999 Sugiyama ............. G06T 7/0012
600/300

(Continued)

FOREIGN PATENT DOCUMENTS

WO WO-2013/058907 A1 4/2013

OTHER PUBLICATIONS

International Search Report and Written Opinion in corresponding International Application No. PCT/US2014/056891, dated Dec. 23, 2014.

*Primary Examiner* — Greta Robinson
(74) *Attorney, Agent, or Firm* — Marshall, Gerstein & Borun LLP; Randall G. Rueth

(57) ABSTRACT

A method for automatically diagnosing inherited retinal disease includes receiving a plurality of dissimilar types of data and pre-processing at least one of the plurality of dissimilar types of data to generate a feature vector descriptive of a patient. Further, the method includes, for each of the plurality of dissimilar types of data: (i) comparing portions of the respective type of data or a corresponding feature vector to data in a mutation proven database; (ii) generating a ranked list of matches between the patient and the plurality of patients with known diagnoses; and (iii) storing the ranked list of matches in an output database. A diagnosis routine then aggregates a plurality of ranked lists of matches in the output database to generate a ranked list of genetic diagnoses corresponding to the patient and sends an indication of the ranked list of genetic diagnoses to the end user device.

21 Claims, 12 Drawing Sheets

(56) References Cited

U.S. PATENT DOCUMENTS

| | | | |
|---|---|---|---|
| 9,228,233 B2* | 1/2016 | Kennedy | C12Q 1/6874 |
| 2004/0115646 A1 | 6/2004 | Finkelstein | |
| 2004/0122709 A1* | 6/2004 | Avinash | G06F 19/322 |
| | | | 705/2 |
| 2007/0025606 A1* | 2/2007 | Gholap | G06F 17/30247 |
| | | | 382/128 |
| 2009/0143685 A1* | 6/2009 | Elner | A61B 3/10 |
| | | | 600/476 |
| 2011/0160562 A1 | 6/2011 | de Oliveira e Ramos et al. | |
| 2011/0299034 A1* | 12/2011 | Walsh | A61B 3/102 |
| | | | 351/206 |
| 2012/0102405 A1* | 4/2012 | Zuckerman | G06F 19/363 |
| | | | 715/733 |
| 2013/0184161 A1 | 7/2013 | Kingsmore et al. | |
| 2013/0208245 A1 | 8/2013 | Campbell | |

* cited by examiner

Visual Field Results

[Done Editing] —640

600

Visual Field Right
☐ Peripheral Scotoma
☐ Peripheral Field Constriction
☐ Enlarged Blind Spot
☐ Central Scotoma
☐ Normal

Visual Field Left
☐ Peripheral Scotoma
☐ Peripheral Field Constriction
☐ Enlarged Blind Spot
☑ Central Scotoma
☐ Normal

Visual Field Date (YYYY-MM-DD)
[2005-03-14]

*FIG. 6A*

BCVA Results

[Done Editing] —650

610

BCVA Right
[20/50]
Enter value as 20/(digit) or Any of the following:
Count Fingers
Hand Motions
Light Perception
No Light Perception
Fixes and Follows

BCVA Left
[20/55]
Enter value as 20/(digit) or Any of the following:
Count Fingers
Hand Motions
Light Perception
No Light Perception
Fixes and Follows

BCVA Date (YYYY-MM-DD)
[2005-03-14]

*FIG. 6B*

Original Image

Border Cleared

Final Spots Image

Spots outlined over original image

1200

Patient Analysis Results

Unique Patient Identifier     Date of Birth     Gender

New Patient     1985-02-25     female     1202

Results

<u>Genetic Diagnosis</u>

| Gene | Probability |
|---|---|
| RPGR | 70% |
| RP2 | 21% |
| RHO | 5% |
| ABCA4 | 2% |
| BEST1 | 1% |

SYSTEMS AND METHODS FOR DIAGNOSING INHERITED RETINAL DISEASES

CROSS-REFERENCE TO RELATED APPLICATIONS

This application claims the benefit of U.S. Provisional Application No. 61/881,711, entitled "Systems and Methods for Diagnosing Inherited Retinal Diseases" which was filed on Sep. 24, 2013, the disclosure of which is hereby incorporated herein by reference in its entirety for all purposes.

TECHNICAL FIELD

The present disclosure generally relates to a method for diagnosing retinal diseases and, more particularly, to a method for automated diagnosis of inherited retinal disease.

BACKGROUND

The human retina is a thin layer of neural tissue at the back of the eye that transforms light into electrical signals for the brain. The retina can be divided into distinct regions related to their visual function. These distinct regions are: (i) the posterior pole, where the majority of photoreceptor cells (responsible for central, high acuity color vision) lie; and (ii) the periphery, which includes everything outside the posterior pole. In particular, the posterior pole includes a non-photosensitive structure known as the optic nerve and the macula. Within the center of the macula is a region known as the fovea, which is responsible for nearly all of our high acuity color vision.

The process of diagnosing an inherited retinal disease typically involves recording demographic information about the patient, documenting their ocular and medical history including the age of onset and reported symptoms, evaluating the family history to determine if there is specific genetic mode of transmission that can be distinguished, and performing a clinical evaluation. The clinical evaluation often includes diagnostic testing with a best corrected visual acuity (BCVA) measurement, electroretinography (ERG) measurement, a Goldmann visual field (GVF) measurement, and interpretation of retinal imaging (e.g., optical coherence tomography, fundus autofluorescence, and fluorescein angiography).

Although the diagnostic process is simple in principle, the task is, in practice, an art. A clinician bases a diagnosis on previous experience and knowledge of the existing literature, and, as a result, only a handful of specialists in the United States can effectively diagnose and manage patients with inherited retinal conditions. Moreover, several factors complicate the diagnostic process, because inherited retinal conditions are clinically and genetically heterogeneous. First, variability can arise in the clinical presentation of patients with the same condition. Second, findings between conditions can have considerable overlap, and a clinician must understand which findings are more useful in making the correct diagnosis. Still further, even if the clinician does have a clear understanding of clinical findings and the likely diagnosis, the clinician must be able to use available information to order appropriate genetic testing for molecular confirmation of the diagnosis. This requires additional proficiency in the complicated field of genetics, because multiple genes can cause the same condition.

Confirming a clinical diagnosis with genetic testing is important because such a confirmation can play a vital role in the management and preservation of vision in patients by aiding in the determination of appropriate therapeutic interventions. Currently, however, cost conscious health management organizations demand that clinicians employ the most cost-effective means for diagnosing a patient's condition. The cost of screening a single gene can be anywhere from several hundred to several thousands of dollars. It can, therefore, be cost prohibitive to pursue genetic testing for all genes associated with a particular condition. Also, screening large numbers of genes introduces logistical complexity in the process of diagnosis. Even when multiple genes can be tested at the same time, as in a panel of genes or with whole genome sequencing, determining causative mutations from polymorphisms can be guided by an assessment of the patient's phenotype.

SUMMARY

In one embodiment, a computer-implemented method for automatically diagnosing inherited retinal disease comprises receiving, via a network interface, a plurality of dissimilar types of data from an end user device, the plurality of dissimilar types of data being related to retinal disease and the plurality of dissimilar types of data corresponding to a patient, and pre-processing, with one or more processors, at least one of the plurality of dissimilar types of data to generate a feature vector descriptive of the patient. Further, the method includes, for each of the plurality of dissimilar types of data: (i) comparing, with the one or more processors, portions of the respective type of data or a corresponding feature vector to data in a mutation proven database, wherein the data in the mutation proven database is similar to the respective type of data and wherein the data in the mutation proven database corresponds to a plurality of patients with known genetic diagnoses; (ii) generating, with the one or more processors, a ranked list of matches between the patient and the plurality of patients with known genetic diagnoses; and (iii) storing, with the one or more processors, the ranked list of matches in an output database. Still further, the method includes aggregating, with the one or more processors, a plurality of ranked lists of matches in the output database to generate a ranked list of genetic diagnoses corresponding to the patient, and sending, via the network interface, an indication of the ranked list of genetic diagnoses to the end user device.

In another embodiment, a computer device for automatically diagnosing inherited retinal disease comprises one or more processors and one or more memories coupled to the one or more processors, wherein the one or more memories include computer executable instructions stored therein that, when executed by the one or more processors, cause the one or more processors to: receive, via a network interface, a plurality of dissimilar types of data from an end user device, the plurality of dissimilar types of data being related to retinal disease and the plurality of dissimilar types of data corresponding to a patient, and pre-process at least one of the plurality of dissimilar types of data to generate a feature vector descriptive of the patient. Further, the computer executable instructions cause the one or more processors to, for each of the plurality of dissimilar types of data: (i) compare portions of the respective type of data or a corresponding feature vector to data in a mutation proven database, wherein the data in the mutation proven database is similar to the respective type of data and wherein the data in the mutation proven database corresponds to a plurality of patients with known genetic diagnoses; (ii) generate a ranked list of matches between the patient and the plurality of patients with known genetic diagnoses; and (iii) store the ranked list of matches in an output database. Still further, the computer executable instructions cause the one or more processors to aggregate a plurality of ranked lists of matches in the output database to generate a ranked list of genetic diagnoses corresponding to the patient and send an indication of the ranked list of genetic diagnoses to the end user device.

BRIEF DESCRIPTION OF THE DRAWINGS

FIGS. 6A-6D illustrate screenshots of example entry or upload forms which can be accessed via the detailed patient chart entry form illustrated in FIG. 5.

FIG. 12 illustrates a screenshot of an example results page which can be utilized as part of the method of FIG. 3.

DETAILED DESCRIPTION

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_' is hereby defined to mean . . . " or a similar sentence, there is no intent to limit the meaning of that term, either expressly or by implication, beyond its plain or ordinary meaning, and such terms should not be interpreted to be limited in scope based on any statement made in any section of this patent (other than the language of the claims). To the extent that any term recited in the claims at the end of this patent is referred to in this patent in a manner consistent with a single meaning, that is done for the sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

System Overview

As used herein, the term "fundus" is hereby defined to mean the surface of an organ opposite its opening. A fundus may be a human retina, for example.

Figure 1:
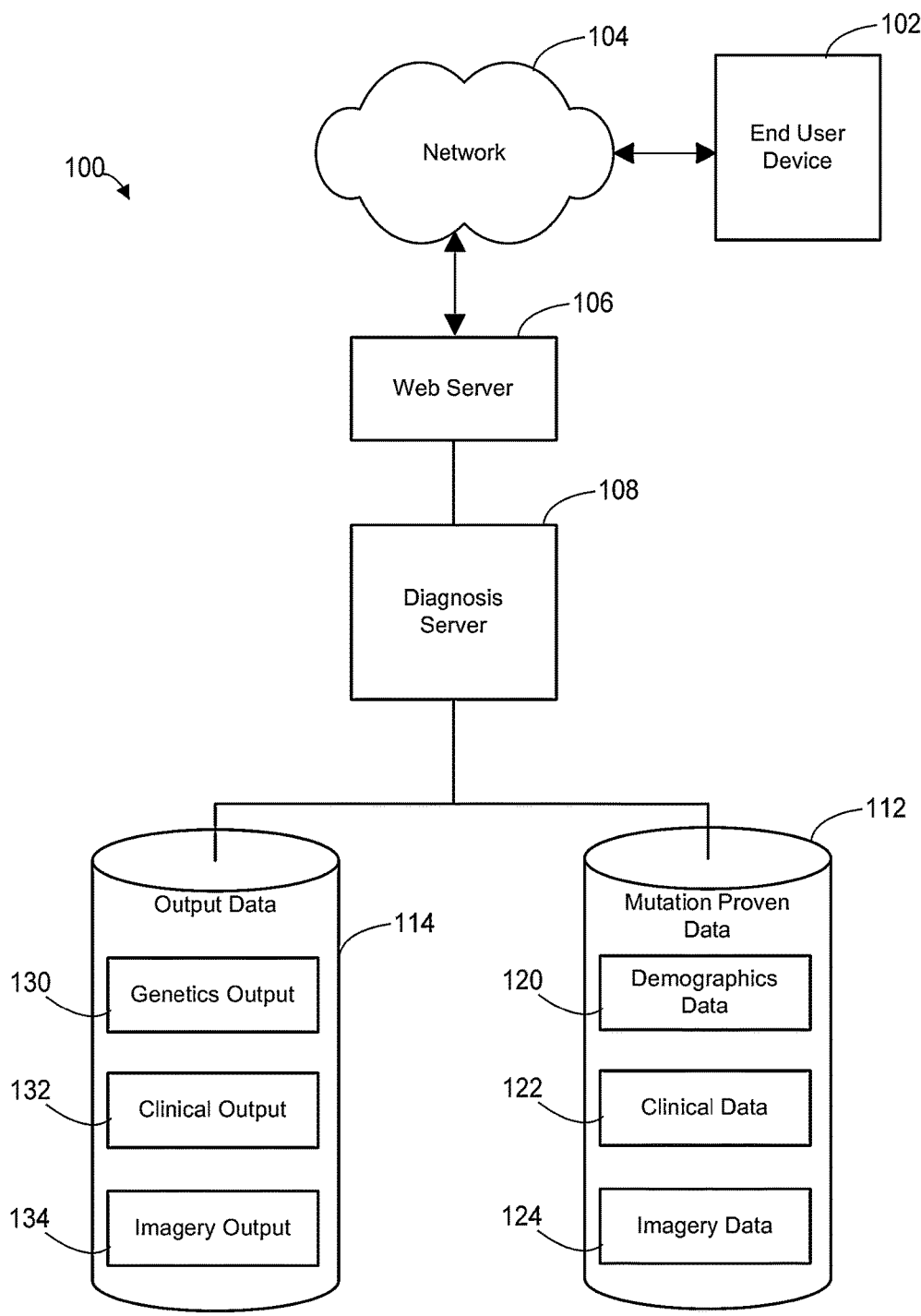
FIG. 1 illustrates an example computing environment for automated diagnosis of inherited retinal disease.

FIG. 1 illustrates an example computing environment 100 to automatically generate diagnoses of inherited retinal disease. A user of an end user device 102 is communicatively coupled, via one or more wired or wireless interfaces, to a network 104 and a web server 106. The end user device may include any suitable computing device such as a personal computer, smartphone, tablet computer, etc. operated by a clinician, for example. The network 104 may be a proprietary network, a secure public internet, a virtual private network or some other type of network, such as dedicated access lines, plain ordinary telephone lines, satellite links, combinations of these, etc. Where the network 104 comprises the Internet, data communications may take place over the network 104 via an Internet communication protocol.

The web server 106 may be implemented in one of several known configurations via one or more servers configured to process web-based traffic received via the network 104 and may include load balancing, edge caching, proxy services, authentication services, etc.

In an implementation, the end user device 102 is capable of executing a graphical interface (GUI) for a retinal disease diagnosis tool within a web browser application, such as Apple's Safari®, Google Android™ mobile web browser, Microsoft Internet Explorer®, etc. The web browser application may be implemented as a series of machine-readable instructions for receiving, interpreting, and displaying web page information from the web server 106 while also receiving inputs (e.g., genetics, clinical, or imagery data) from the user. Further, those skilled in the art will recognize that the present system may be utilized in a dedicated application in addition to a web browser.

A diagnosis server 108 may include a number of software applications responsible for generating retinal disease diagnosis tool content to be included in the web pages sent from the web server 106 to the end user device 102. For example, the diagnosis server 108 may generate data input forms (e.g., for input of clinical data and imagery data about a patient), diagnosis results tables, disease trend indications, etc. as discussed below, to be included in the web pages sent to the end user device 102. The details of an implementation of the diagnosis server 108 are discussed in more detail with reference with FIG. 2. Further, although FIG. 1 illustrates one diagnosis server 108, the techniques of the present disclosure may be implemented by any number of servers with any number of processors, such as in a "cloud computing" implementation.

The example diagnosis server 108 is operatively connected to a mutation proven database 112 and an output database 114. However, it should be noted that, while not shown, additional databases may be operatively connected to the diagnosis server 108 and/or the databases 112 and 114 may be combined or split into any number of databases or data structures.

The mutation proven database 112 may be, for example, configured to store data about a plurality of patients with known genetic diagnoses. The data about the plurality of patients may include: (i) a plurality of demographic data 120 such as age, sex, etc.; (ii) a plurality of clinical data 122 such as ERG values, visual field information, visual acuity information, etc.; and (iii) a plurality of imagery data 124 such as autofluorescence (AF), Optical Coherence Tomography (OCT), or color images in any suitable format (TIF, JPG, PNG, etc.). In one implementation, the mutation proven database 112 includes a list of patient identifications (IDs) and corresponding entries (e.g., demographic, clinical, and imagery entries) for each patient ID. It is understood, however, that the mutation proven database 112 may include any suitable type of data related to known genetic diagnoses, and the mutation proven database 112 may be organized according to any appropriate data structure.

The output database 114 may be, for example, configured to store results or output generated as part of an automated diagnosis of inherited retinal disease. The results stored in the output database 114 may include: (i) genetics output 130 (or "mode of transmission" output) such as generated probabilities corresponding to various genetic forms of transmission and based on family history data about a patient; (ii) clinical output 132 such as clinical feature vectors representative of clinical data (e.g., ERG values) about the patient and/or ranked lists of genetic diagnoses based on clinical data about the patient; and (iii) imagery output 134 such as imagery feature vectors representative of imagery data (e.g., AF images) and/or ranked lists of genetic diagnoses based on imagery data about the patient. Further, the output database 114 may store a final ranked list of genetic diagnosis based all the data about a patient (e.g., including both clinical and imagery data about a patient). The generation, storing, and utilization of genetics, clinical, and imagery output is further discussed with reference to FIG. 3.

Figure 2:
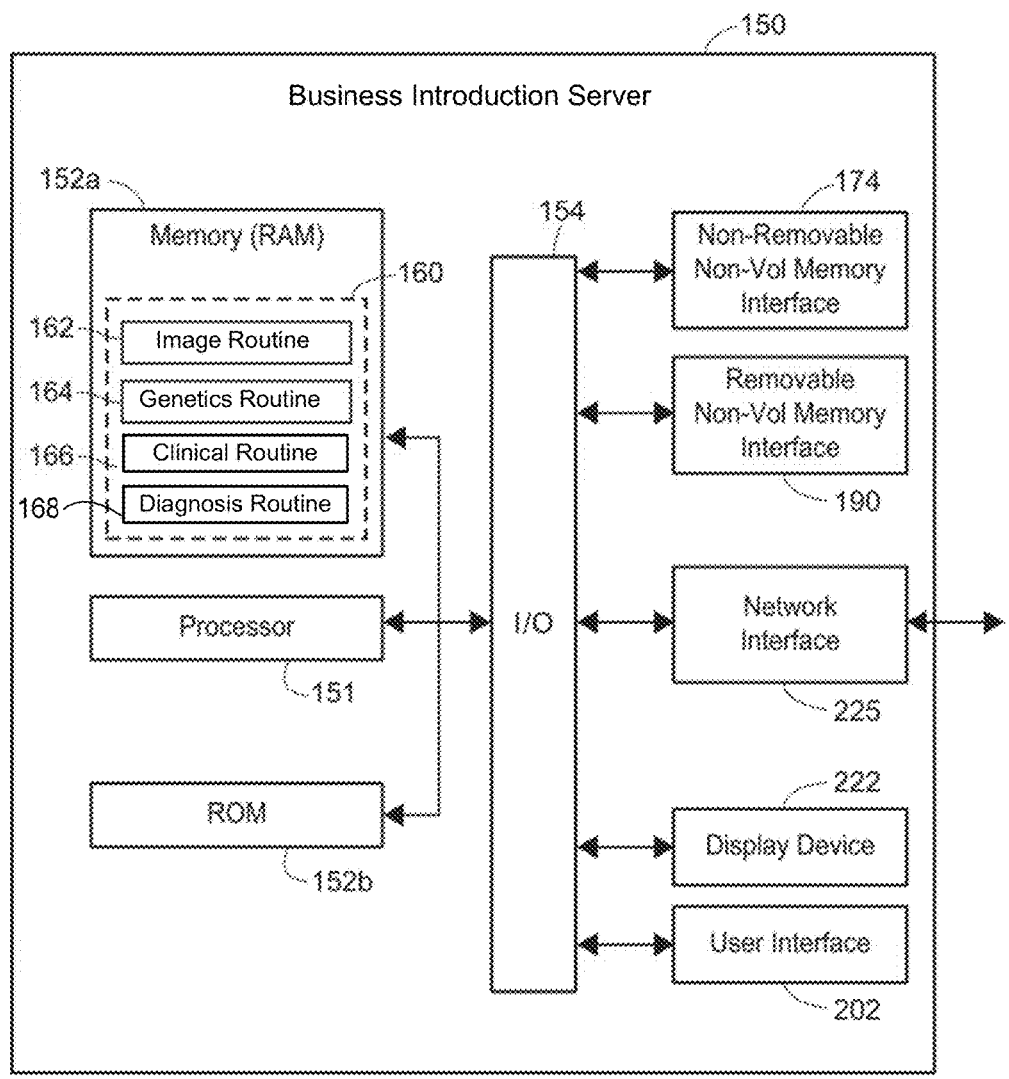
FIG. 2 is a block diagram of an example implementation of the diagnosis server illustrated in FIG. 1.

FIG. 2 illustrates an example diagnosis server 150 that may automatically generate diagnoses of inherited retinal disease and generate content for display on an end user device. The diagnosis server 150 may be implemented as the diagnosis server 108 in the example computing system 100, for example. The diagnosis server 150 may include one or more processing units, 151, a system memory, 152a and 152b, and a system bus 154 that couples various system components including the system memory 152 to the processing units 151. The system bus 154 may include an Industry Standard Architecture (ISA) bus, a Micro Channel Architecture (MCA) bus, Enhanced ISA (EISA) bus, Video Electronics Standards Association (VESA) local bus, a Peripheral Component Interconnect (PCI) bus or a Mezzanine bus, and the Peripheral Component Interconnect Express (PCI-E) bus.

The diagnosis server 150 may include an assortment of computer-readable media. Computer-readable media may be any media that may be accessed by the diagnosis server 150. By way of example, and not limitation, the media may include both volatile and nonvolatile media, removable and non-removable media. Media may also include computer storage media and communication media. Computer storage media may include volatile and nonvolatile, removable and non-removable media that stores information such as computer-readable instructions, program modules, data structures, or other data. Computer-storage media may include RAM, ROM, EEPROM, or other memory technology, optical storage disks, magnetic storage devices, and any other medium which may be used to store computer-accessible information. Communication media may be computer-readable instructions, data structures, program modules, or other data in a modulated data signal or other transport mechanism. Communication media may include wired media such as a wired network or direct-wired connection, and wireless media such as RF, infrared, and other wireless media.

The system memory may include storage media in the form of volatile and/or non-volatile memory such as ROM 152a and RAM 152b. A basic input/output system (BIOS), containing algorithms to transfer information between components within the computer 150, may be stored in ROM 152b. Data or program modules that are immediately accessible or are presently in use by the processing units 151 may be stored in RAM 152a. Data normally stored in RAM 152a while the diagnosis server 150 is in operation may include an operating system, application programs, program modules, and program data. In particular, the RAM 152a may store a retinal disease diagnosis application 160 including an image routine 162, a genetics routine 164, a clinical routine 166, and a diagnosis routine 168, for example.

The diagnosis server 150 may also include other storage media such as a hard disk drive that may read from or write to non-removable, non-volatile magnetic media, a magnetic disk drive that reads from or writes to a removable, non-volatile magnetic disk, and an optical disk drive that reads from or writes to a removable, nonvolatile optical disk. Other storage media that may be used includes magnetic tape cassettes, flash memory cards, digital versatile disks, digital video tape, solid state RAM, and solid state ROM. The hard disk drive may be connected to the system bus 154 through a non-removable memory interface such as interface 174. A magnetic disk drive and optical disk drive may be connected to the system bus 154 by a removable memory interface, such as interface 190.

A user may interact with the diagnosis server 150 through input devices such as a keyboard or a pointing device (i.e., a mouse). A user input interface 202 may be coupled to the system bus 154 to allow the input devices to communicate with the processing units 151. A display device 222, such as a monitor, may also be connected to the system bus 154 via a video interface (not shown).

The diagnosis server 150 may operate in a networked environment using logical connections to one or more remote computing devices, such as end user device 102 or web server 106, for example. The remote computing device may be a personal computer (PC), a server, a router, or other common network node. The remote computing device typically includes many or all of the previously-described elements regarding the diagnosis server 150, even though such elements are not illustrated in the remote computing devices of FIG. 1. Logical connections between the diagnosis server 150 and one or more remote computing devices may include a wide area network (WAN). A typical WAN is the Internet. When used in a WAN, the diagnosis server 150 may include a modem or other means for establishing communications over the WAN. The modem may be connected to the system bus 154 via the network interface 225, or other mechanism. In a networked environment, program modules depicted relative to the diagnosis server 150, may be stored in the remote memory storage device. As may be appreciated, other means of establishing a communications link between the computer 150 and a remote computing device may be used.

Automated Diagnosis of Inherited Retinal Disease

Figure 3:
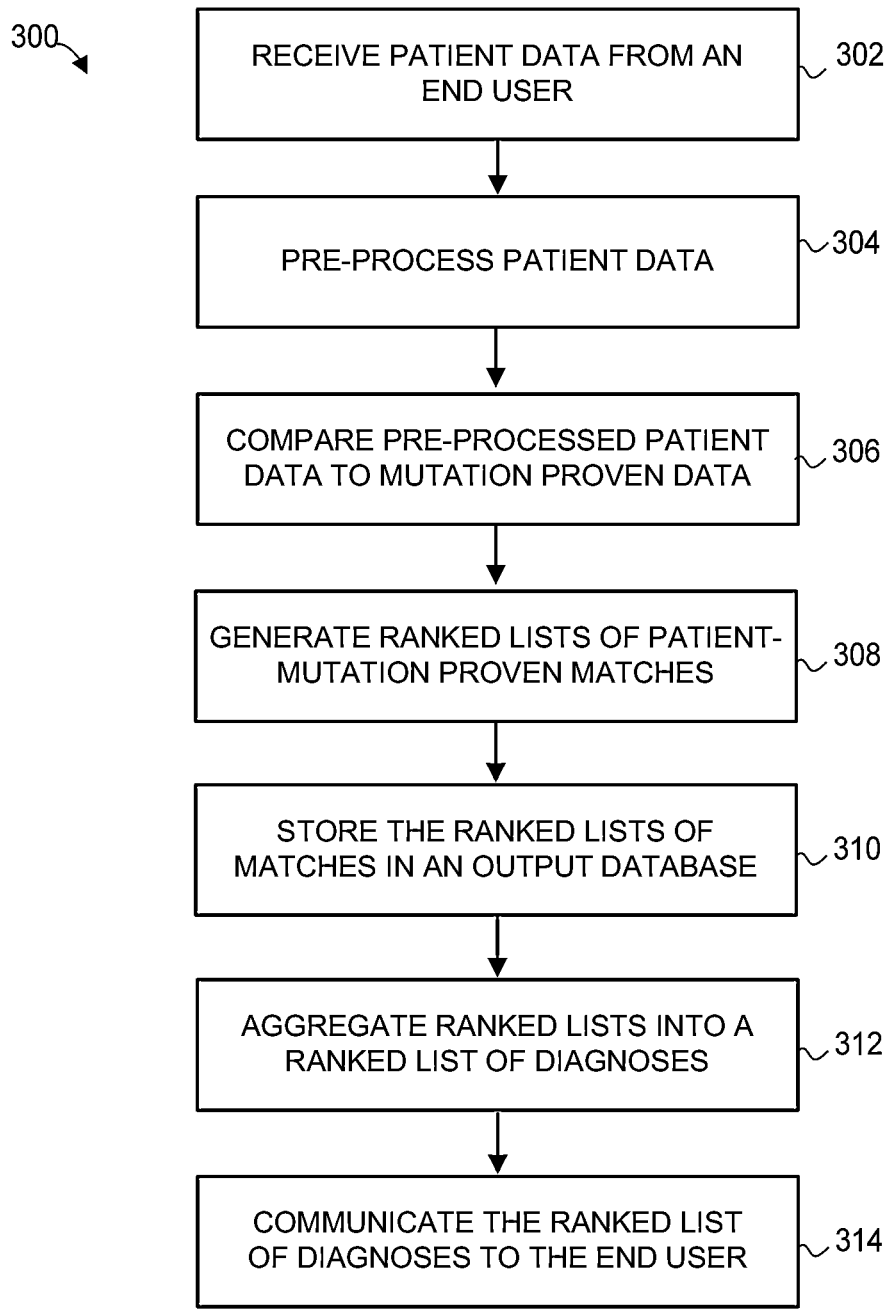
FIG. 3 is a flow diagram of an example method for automated diagnosis of inherited retinal disease which can be implemented by the diagnosis server illustrated in FIG. 2.

FIG. 3 is a flow diagram of an example method 300 for automatically diagnosing inherited retinal disease. The method 300 may be implemented by the diagnosis server 108, for example. To aid in the description of the method 300, example screenshots, illustrated in FIGS. 4, 5, 6A-6D, 7, 8, and 12, are referred to below. However, it is understood that a diagnosis server may utilize any suitable web browser or application based content and interaction to facilitate the automatic diagnosis of inherited retinal disease. Further, elements of FIG. 1 are referred to in the description of the method 300, but, of course, the method 300 may be implemented in any suitable computing environment.

To begin, patient data is received from an end user device (block 302). For example, a clinician may operate the end user device 102 to input patient data via a web browser application and subsequently send the patient data to the diagnosis server 108. The patient data may include multiple dissimilar types of data related to inherited retinal disease. By way of example and without limitation, the patient data may include: (i) family history data, such as number and gender of children, number of brothers and sisters, number of paternal and maternal aunts and uncles, parents, and grandparents, who, if any, is affected by disease, the age of onset of disease in each individual, and whether or not there is consanguinity between the patient's parents; (ii) demographic data, such as age, sex, ethnicity, etc.; (iii) clinical data such as Best Corrected Visual Acuity (BCVA), visual field, ERG measurements, and electrooculography (EOG) measurements; and (iv) imagery data, such as AF, color, and OCT images of the retina. In general, a clinician may input, and a diagnosis server may receive, any number and/or combination of types of data related to inherited retinal disease.

Figure 4:
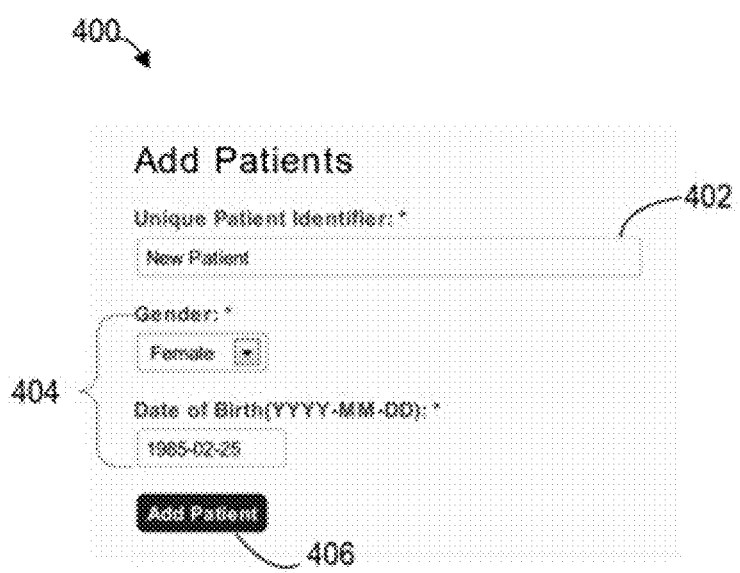
FIG. 4 illustrates a screenshot of an example landing page 400 which can be utilized as part of the method of FIG. 3.

FIG. 4 illustrates a screenshot of an example landing page 400, accessed via a web browser application, in which a clinician may begin to input patient data and subsequently send the patient data to a diagnosis server for evaluation. The landing page 400 may include multiple form fields in which a clinician may input information about a patient. For example, the clinician may input a "Nickname" (e.g., "New Patient") for the patient into a nickname form field 402 and sex and age information into one or more demographics form fields 404. The clinician may send entered patient data to the diagnosis server 108 by selecting (e.g., via a click or tap) the add patient button 406. In some implementations, selection of the add patient button 406 will also register the patient (e.g., under the nickname "New Patient") in a list of patients (not shown), such that corresponding patient data may be later accessed by the clinician.

Figure 5:
FIG. 5 illustrates a screenshot of an example detailed patient chart entry form which can be utilized as part of the method of FIG. 3.
Figure 6C:
Figure 6D:
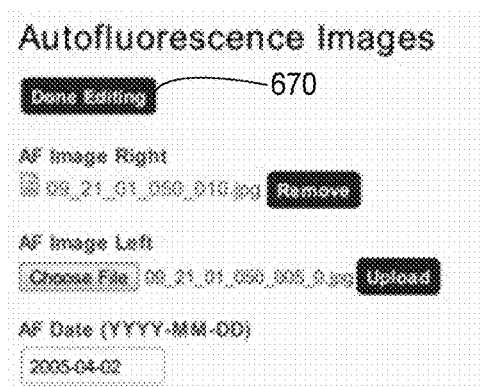
Figure 7:
FIG. 7 illustrates a screenshot of an example completed patient chart entry form which can be a completed version of the detailed patient chart entry form illustrated in FIG. 5.

Alternatively, or in response to selection of the add patient button 406, the clinician may be presented with a detailed patient chart entry form 500, as illustrated in FIG. 5. The clinician may use the detailed patient chart entry form 500 to enter or upload a variety of dissimilar types of patient data (BCVA, ERG, etc.) and subsequently send the entered or uploaded patient data to the diagnosis server 108. For example, the patient chart entry form 500 may include a visual field entry section 502, a BCVA results entry section 504, an ERG results entry section 506, an AF images upload section 508, and a color images upload section 510. In addition, each of the sections 502, 504, 506, 508, and 510 may have a corresponding selectable button (buttons 512, 514, 516, 518, and 520, respectively) which the clinician may select to enter patient data corresponding to each data type (visual field, BCVA, ERG, AF imagery, and color imagery).

FIGS. 6A-6D illustrate screenshots of example entry forms accessible via selecting one of the buttons 512, 514, 516, 518, and 520. For example, a web browsing application may present a clinician with a visual field entry form 600 in response to the selection of the button 512, a BCVA entry form 610 in response to the selection of the button 514, an ERG entry form 620 in response to the selection of the button 516, and an AF image upload form 630 in response to selection of button 518. The example entry forms 600, 610, and 620 and the example upload form 630 may include any suitable interfaces for the entry or upload of patient data, such as numerical/text/date entry boxes, radio button, buttons triggering file browsing interfaces, etc. After entering or uploading patient data via one of the entry forms 600, 610, or 620 or the upload form 630, a clinician may select one of the respective done editing buttons 640, 650, 660, or 670 to send the entered or uploaded data (e.g., AF images) to the diagnosis server 108. Further, upon sending patient data to the diagnosis server 108, the clinician may be presented with or may have access to a summary of the entered patient data, such as the summary page 700 illustrated in FIG. 7.

Returning to FIG. 3, after receiving patient data (e.g., via a clinician interacting with a web browsing application), at least some of the entered or uploaded patient data is pre-processed (block 304). By way of example, the pre-processing of (A) imagery data, (B) family history data, and (C) clinical data is discussed below. However, it is understood that any type of data related to inherited retinal disease may be pre-processed to transform the data into a convention form.

(A) With regard to uploaded imagery data corresponding to a patient, such as AF, OCT, and color images, the diagnosis server 108 may execute the image routine 162 to automatically identify, quantify, and categorize pathological markers of retinal disease based on uploaded images. Further, the diagnosis server 108 may execute the image routine 162 to transform the quantifications and categorizations of pathological markers into one or more feature vectors.

In one implementation, the diagnosis server 108 uses image processing methods to ensure that uploaded images are directly comparable with one another, with respect to quality, contrast, and gain. Such a process may involve applying a non-linear transformation to some or all of the pixels of an image to compensate for differences in imaging sensor positioning, and illumination conditions. Then, the diagnosis server 108 may apply an additional non-linear function in an attempt to normalize the input images with respect to one another. For example, the image routine 162, when executed by the diagnosis server 108 may use segmentation or histogram shifting in an attempt to normalize a set of uploaded images.

Figure 8:
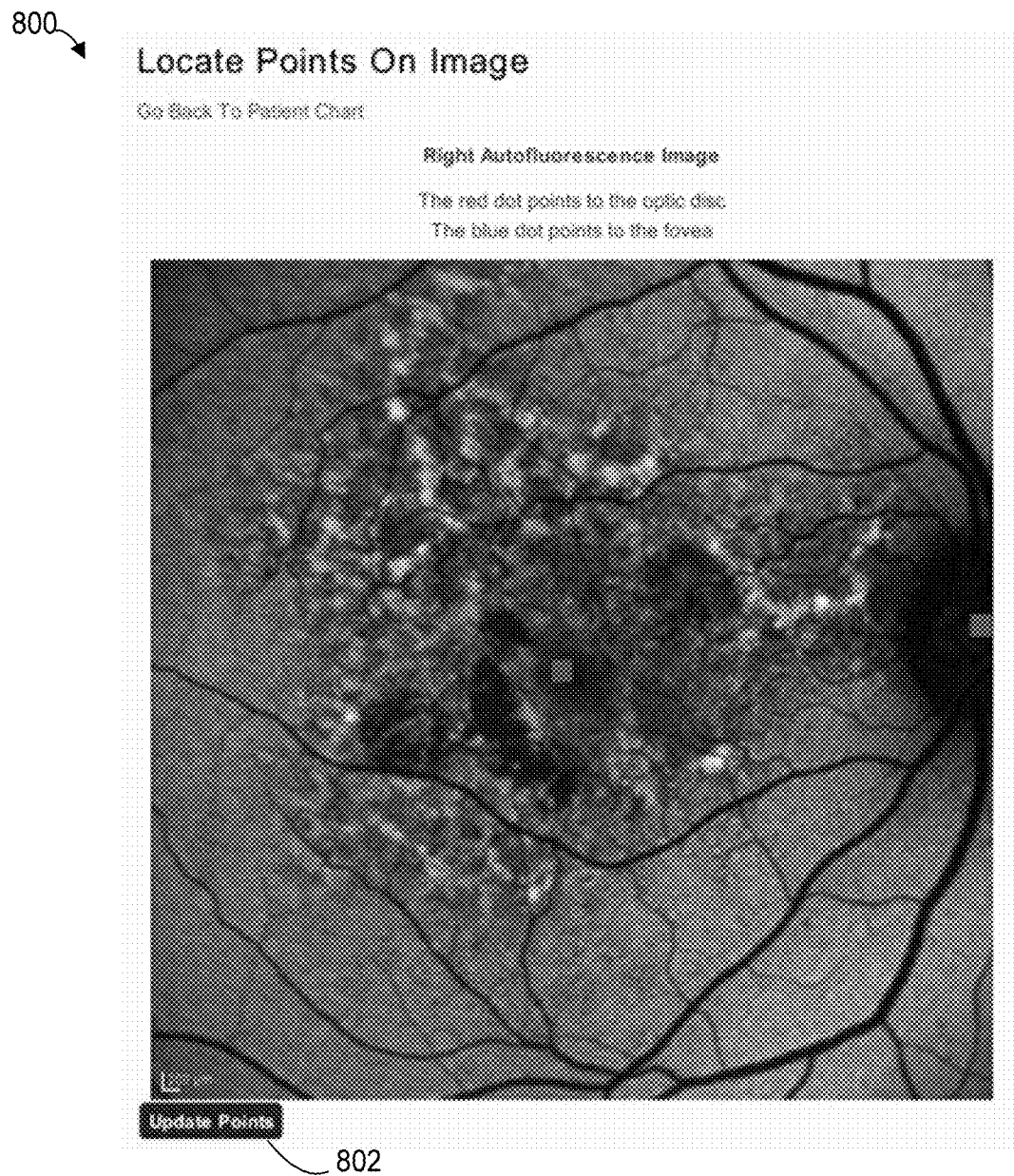
FIG. 8 illustrates a screenshot of an example labeling interface which can be utilized as part of the method of FIG. 3.

Image pre-processing may also involve determining regions in each image to evaluate based on the locations of the fovea and optic disc. In order to facilitate such a determination, the diagnosis server 108 may prompt a user (e.g., a clinician) to label the location of multiple structures in the eye on a representative uploaded image via a browser-based label interface. FIG. 8, for example, illustrates a screenshot of a labeling interface 800 displayed within a web browser. In the labeling interface 800, a clinician may select (e.g., via a click or tap) a location of the fovea and optic disc. Once selected, the clinician may click on the update points button 802 to send indications of the selected locations to the diagnosis server 108.

The example image routine 162 may use indicated locations of the fovea and optic disc to determine the location of the macula, in an implementation. Subsequently, the image routine 162 may utilize the location of the macula, and hence regions outside the macula, in the application of certain filters. Although input of the fovea and optic disc locations via clinician interaction is discussed above, it should be noted that an image routine may use computer vision techniques to automatically detect the location of the fovea and optic disc. Even if a clinician manually indicates the location of either the fovea and/or the optic disc, the image routine 162 may still execute an automated technique to refine and validate such input.

Figure 9:
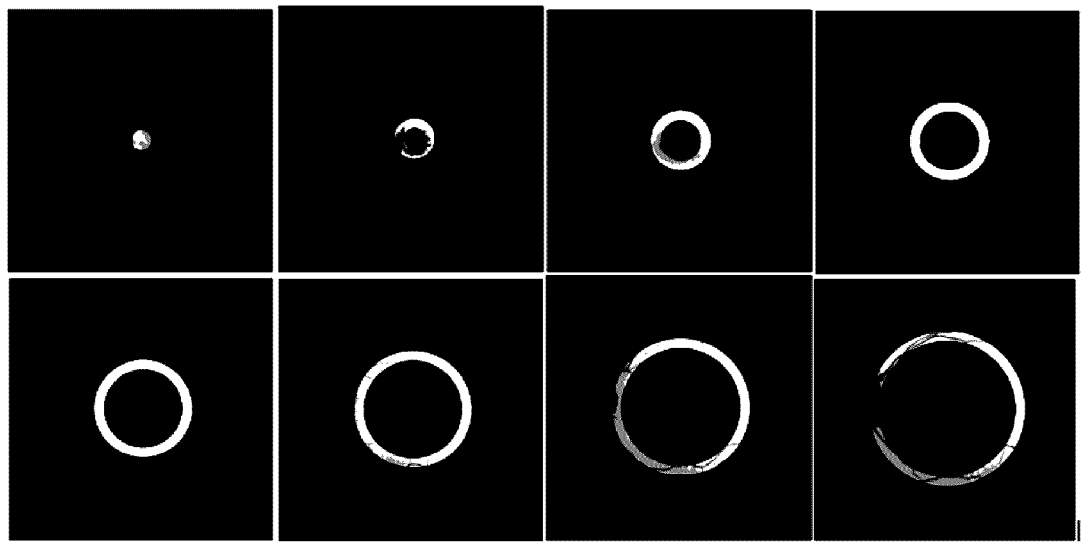
FIG. 9 is an example array of hyperfluorescent rings in autofluorescence imaging.

In some implementations, image pre-processing may include an analysis on four distinct features: (i) the presence or absence of discrete hypofluorescent marks outside the macula; (ii) the presence or absence of hypofluorescence encompassing the macula; (iii) the presence or absence of hyperfluorescent marks outside the macula; and (iv) the presence or absence of a hyperfluorescent ring surrounding the macula (see example ring images included in FIG. 9). Such an analysis may include an objective quantification of these features such as the quantification discussed in U.S. Provisional Application No. 61/858,915 entitled "Automated measurement of changes in retinal, retinal pigment epithelial, or choroidal disease" and filed on Jul. 26, 2013, the entire disclosure of which is hereby incorporated by reference herein. Other methods of object detection may include the analysis of image texture, in some implementations. This analysis of image texture may involve a convolution of images with a sliding window detector, where the sliding window detector incorporates functions that respond uniquely to different spatial frequencies of intensity variation, for example. Further, the image routine 162 may utilize edge detection methods to delineate detected objects represented by consistent areas of a specific texture. Such edge detection methods may utilize established algorithms such as an Active contour model (snakes), Curvelet transforms, or Gabor wavelets, for example.

Figure 10:
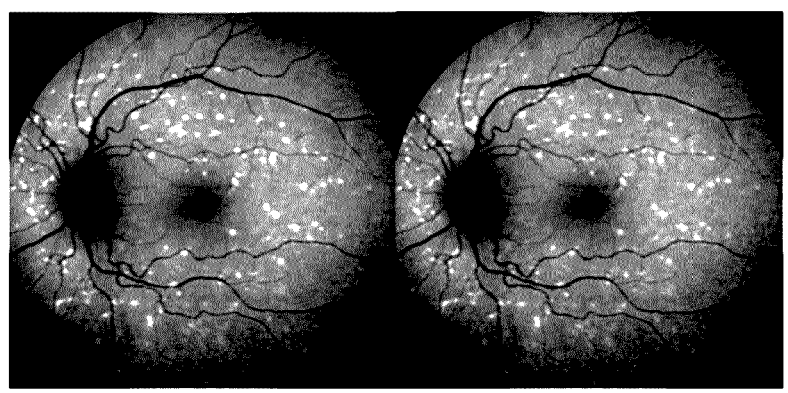
FIG. 10 is an example image with hyperfluorescent flecks in autofluorescence imaging.
Figure 11:
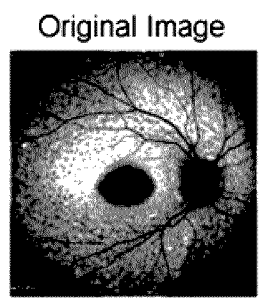
FIG. 11 is an example image with hyporfluorescent flecks in autofluorescence imaging.
Figure 11:
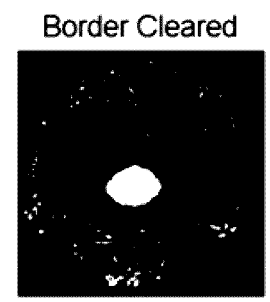
Figure 11:
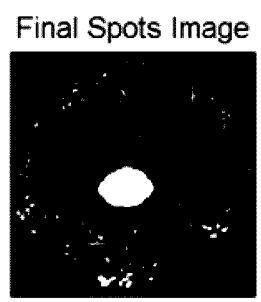
Figure 11:
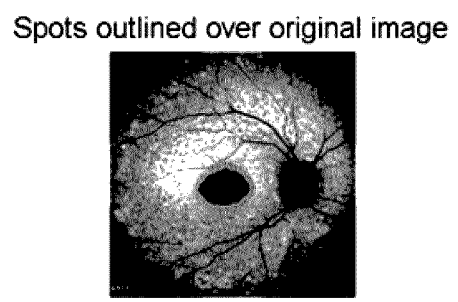

In another implementation, image pre-processing may include the extraction of other clinically relevant features. For example, in fundus AF, hyperfluorescent flecks and hypofluorescent flecks (see FIG. 10 for an example image with hyperfluorescent flecks and see FIG. 11 for an example image with hypofluorescent flecks) are distinguishing features of different retinal dystrophies. The image routine 162 may extract these features using a combination of object detection methods to identify blobs, flecks, drusen deposits, and any other additional clinically related features.

As an output of image pre-processing, the image routine 162 may generate one or more feature vectors representing the imagery data about the patient. For example, the feature vectors may include indications of the total area of hyperfluorescence and/or hypofluorescence. These "features" may, in some implementations, be represented by bounded continuous values. However, in other implementations, the image routine 162 may transform image features to discrete Boolean values (e.g., via hyperfluorescent or hyperfluorescent indications compared, or paired, one or more threshold values).

The image routine 162 may store image feature vectors, representative of the imagery data corresponding to the patient, in a database, such as the output database 114. In this manner, the image routine 162 or other routines of the diagnosis server 108 may access the image feature vectors later in the flow of method 300.

(B) With regard to uploaded family history data corresponding to a patient, the diagnosis server 108 may execute the genetics routine 164 to generate probabilities corresponding to genetic modes of transmission.

In one implementation, the genetics routine 164, when executed by the diagnosis server 108, compares provided family history data to stored rules (e.g., stored in the memory 152*a*) regarding a variety of modes of transmission. As part of the comparison, the genetics routine 164 may compute a probability of each genetic mode of transmission. By way of example, modes of transmission which may be assessed by the genetics routine 164 include autosomal dominant transmission, autosomal recessive transmission, X-linked recessive transmission, and a simplex case, and the corresponding rules may be based on clinically accepted probabilities or averages.

As an output, the genetic routine 164 may generate a numeric probability score corresponding to the transmission of a particular genetic disorder. For example, the genetic routine 164 may store numeric probabilities in a database, such as the output database 114.

(C) With regard to uploaded clinical data corresponding to a patient, the clinical routine 166, when executed by the diagnosis server 108, may generate a clinical feature vector representative of the patient whose patient data has been received by the diagnosis server 108.

In some implementations, clinical data received at block 302 includes a plurality of clinical parameters, such as ERG parameters (or measurements), visual acuity parameters, and visual field parameters. Based on these parameters, the clinical routine 166 may calculate bounded continuous values and/or discrete Boolean values. For example, ERG parameters are natively a continuous variable, and, therefore, the clinical routine 166 may only normalization the numeric ERG parameters to correct for age and equipment variability.

Visual acuity (or BCVA) has corresponding descriptive (e.g., 20/50), rather than numeric, parameters. Thus, the clinical routine 166 may translate visual acuity parameters to a known continuous scale, such as the Logarithm of Minimum Angle of Resolution (logMAR) scale. Visual field, on the other hand, is a feature based description (central scotoma, enlarged optic nerve scotoma, decreased range, etc.). To translate this feature based description, the clinical routine 166 may generate a Boolean representation. For example, the Boolean vector of {True,False,True, . . . } may represent features that are present in a visual field such as peripheral visual field constriction (e.g., True in this case), central scotoma at the macula (e.g., False in this case), enlarged scotoma at the optic nerve (e.g., True in this case), etc.

A Boolean representation will allow for later comparison to data in the mutation proven database 112, which may have patient information that has been tagged in an identical manner, in an implementation. For example, a routine may compare two given clinical feature vectors with paired True-False values at the same position value in each vector. Such a comparison is further discussed with reference to block 308.

Further, clinical feature vectors and modes of genetic transmission may be combined to create a single feature vector that is representative of the patient whose clinical data has been input into the system, in an implementation. For example, the clinical routine 166 may utilize numeric probabilities of genetics modes of transmission (e.g., generated from family history data) to weight and combine various feature vectors generated from clinical data (e.g., a BCVA feature vector, a visual field feature vector, and an ERG feature vector).

As an output, the clinical routine 166 may generate one or more numeric or Boolean based feature vectors representing the patient's clinical data. For example, the clinical routine 166 may store continuous/Boolean vectors in a database, such as the output database 114.

Returning now to FIG. 3, after pre-processing of the patient data, representations of clinical, demographic, and imagery data (e.g., feature vectors corresponding to the respective type of data or portions of the data itself) are compared with data in the mutation proven database 112.

For example, the diagnosis routine 168 (executed by the diagnosis server 108) may query the mutation proven database 112 against a numerical clinical feature vector, or, in the case of a Boolean feature vector, the diagnosis routine 168 may compare two given feature vectors whose True-False values are paired. Likewise, the diagnosis routine 168 may compare image feature vectors showing specific disease markers to records in the mutation proven database 112 corresponding to images tagged with disease markers.

As a result of the comparison with the mutation proven database 112, ranked lists of mutation proven patients are generated (block 308). For example, a comparison of a clinical feature vector with data in the mutation proven database 112 may return a ranked list of "nearest neighbors" to the clinical feature vector. In one implementation, the diagnosis routine 168 may execute an approximate nearest neighbor search in an arbitrarily high dimensional space, or other suitable machine learning routine, to identify the entries (i.e., known patients with proven genetic diagnoses) in the mutation proven database 112 that have similarities with the clinical/imagery data about the patient and corresponding distances between the patient and the entries in the mutation proven database 112.

In some implementations, ranked lists of matches in the mutation proven database may be ordered lists, whereas, in other implementation, ranked lists of matches may be sorted according to corresponding probabilities. Further, the diagnosis routine 168 may generate one or more ranked lists of matches in the mutation proven database 112 for each of the types of data received at block 302. For example, a ranked list of matches may be generated for each of an imagery feature vector, a clinical feature vector, and a plurality of demographic information. The ranked lists of matches may be stored in corresponding data structures of the output database 114, such as in the clinical output 132 and the imagery output 134 (block 310)

Next, multiple ranked lists of matches to proven genetic diagnoses (e.g., one list corresponding to clinical data and one list corresponding to imagery data) are weighted and combined to produce a final ranked listed of genetic diagnoses (block 312). The weights used to combine multiple ranked lists into a final ranked list of genetic diagnoses may be at least partially based on human input (e.g., via weighting of parameters) from clinicians with expertise in inherited retinal diseases. However, the weights used to generate the final ranked list of genetic diagnoses may be refined over time based on further accumulated data in the mutation proven database 112 and/or based on further learning of algorithms. For example, expert clinicians may initialize the diagnosis routine 168 with certain weights based on clinical experience. Then, as the diagnosis routine 168 is verified, the weights of the diagnosis routine 168 may be refined. In general, the diagnosis routine 168 may use any suitable supervised or unsupervised machine learning technique to update weights in light of verification results and/or newly accumulated data.

Because of the collective and flexible nature of the method 300, the method 300 may accommodate variable degrees of input data. If, for example, visual field data is unavailable, the diagnosis routine 168 may still calculate the most likely genetic diagnoses based on other available information, such as BCVA or ERG data. In general, the method 300 may utilize any amount and combination of dissimilar types of data related to inherited retinal disease.

The diagnosis routine 168 may generate the final ranked list of genetic diagnoses as an ordered list of genetic diagnoses, or the diagnosis routine 168 may calculate a numeric probability (e.g., 90%) corresponding to each genetic diagnosis in the list of genetic diagnoses. As with the weights, the algorithms employed by the diagnosis routine 168 to generate such probabilities may include machine learning algorithms that may be refined after verification and the accumulation of additional data.

Finally, the final ranked list of likely genetic diagnoses is sent to the end user device, operated by the clinician, to provide an indication of likely causative genes and/or gene mutations corresponding to the patient (block 312). For example, the ranked list of genetic diagnoses may be sent to the end user device as a table of genes and corresponding probabilities ordered according to descending probability. Subsequently, a clinician may utilize such a ranked list of genetic diagnoses as a guide for genetic screening, such as prioritizing genes for consideration in whole exome sequencing or whole genome sequencing.

Thus, the method 300, may aid clinicians in rapidly and efficiently diagnosing a patient's retinal condition and guiding genetic testing strategies. For example, a clinician operating the end user device 102 may both rapidly exploit a variety of dissimilar types of data and reduce the logistical complexity of having to screen a large number of genes. Further, the method 300 may provide a clinician sufficient automated capabilities to consider a plurality of likely retinal diseases, even in the absence of specialized medical training in inherited retinal diseases.

For clarity, FIG. 12 illustrates a screenshot of an example results page 1200 that may be presented to a clinician (e.g., within a web browser) after a ranked list of genetic diagnoses is sent to the end user device 102. The results page includes a brief summary 1202 of information about the patient and a table 1204 of gene-probability pairs. In this example case, the genes are represented by a corresponding gene name (RPGR, RP2, etc.), and the table 1204 may only include genes with a probability, or likelihood, of 1% or greater. However, it is understood that a ranked list of genes may be presented to a clinician in any suitable representation, such as a pie chart, graph, bar chart, list, etc.

Moreover, in some implementations, at least some of the diagnoses in a ranked list of genetic diagnoses presented to a clinician may be selectable by the clinician. In this manner, the clinician may view further information about the diagnosis. For example, the diagnosis server 108 may generate diagnosis summaries corresponding to each of the diagnoses in a ranked list of genetic diagnoses and based on data in the mutation proven database. For example, the diagnosis server 108 may generate a diagnosis summary with trends indicating implications of a particular diagnosis on patients matching the demographics of the patient whose information is under consideration. In general, such summaries may include any representative information about a diagnosis, such as medical book excerpts, parameter trends (e.g., ERG and BCVA trends), exemplary images, etc.

We claim:

1. A computer-implemented method for automatically diagnosing inherited retinal disease, the method comprising:
receiving, via a network interface, a plurality of dissimilar types of data from an end user device, the plurality of dissimilar types of data being related to retinal disease and the plurality of dissimilar types of data corresponding to a patient;
pre-processing, by one or more processors, at least one of the plurality of dissimilar types of data to generate a feature vector descriptive of the patient;

for each of the plurality of dissimilar types of data:
comparing, by the one or more processors, portions of the respective type of data or a corresponding feature vector to data in a mutation proven database, wherein the data in the mutation proven database is similar to the respective type of data and wherein the data in the mutation proven database corresponds to a plurality of patients with known genetic diagnoses,
generating, by the one or more processors, a ranked list of matches between the patient and the plurality of patients with known genetic diagnoses, and
storing, by the one or more processors, the ranked list of matches in an output database,
aggregating, by the one or more processors, a plurality of ranked lists of matches in the output database to generate a ranked list of genetic diagnoses corresponding to the patient; and
sending, via the network interface, an indication of the ranked list of genetic diagnoses to the end user device.

2. The computer-implemented method of claim 1, wherein the plurality of dissimilar types of data includes at least two of demographic data, retinal imagery data, or clinical data about the patient.

3. The computer-implemented method of claim 1, wherein the plurality of dissimilar types of data includes demographic data, retinal imagery data, and clinical data about the patient.

4. The computer-implemented method of claim 1, wherein the plurality of dissimilar types of data includes a plurality of images of the retina.

5. The computer-implemented method of claim 4, further comprising executing, by the one or more processors, an image routine to:
identify pathological markers of retinal disease within each of the plurality of images of the retina,
quantify the pathological markers of retinal disease by aligning the plurality of images of the retina and collectively analyzing the aligned plurality of images of the retina, and
categorize the pathological markers of retinal disease into categories each indicative of a particular retinal dystrophy.

6. The computer-implemented method of claim 1, wherein pre-processing at least one of the plurality of dissimilar types of data to generate the feature vector includes generating an imagery feature vector descriptive of the identified, quantified, and categorized pathological markers of retinal disease.

7. The computer-implemented method of claim 6, wherein the features of the image feature vector are transformed to discrete Boolean values.

8. The computer-implemented method of claim 1, further comprising receiving, via a network interface, family history data.

9. The computer-implemented method of claim 8, further comprising executing, by the one or more processors, a genetics routine to:
determine a possible diagnosis based on the family history data,
generate a probability corresponding to the possible diagnosis, and
store the probability corresponding to the possible diagnosis in the output database.

10. The computer-implemented method of claim 9, wherein determining a possible diagnosis and generating a probability corresponding to the possible diagnosis includes detecting the presence or absence of a form of transmission in the family history data.

11. The computer-implemented method of claim 10, wherein the form of transmission is at least one of autosomal dominant transmission, autosomal recessive transmission, X-linked recessive transmission, or a simplex case.

12. The computer-implemented method of claim 9, wherein the plurality of dissimilar types of data includes clinical data and wherein pre-processing at least one of the plurality of dissimilar types of data to generate the feature vector includes:
converting each of a plurality of clinical parameters in the clinical data to a score, and
combining scores corresponding to the plurality of clinical parameters with the probability corresponding to the possible diagnosis to generate the clinical feature vector representative of the clinical data and the family history data.

13. The computer-implemented method of claim 12, wherein combining scores corresponding to the plurality of clinical parameters with the probability corresponding to the possible diagnosis at least partially based on the probability corresponding to the possible diagnosis.

14. The computer-implemented method of claim 1, wherein aggregating the plurality of ranked lists of matches in the output database to generate the ranked list of genetic diagnoses corresponding to the patient includes:
assigning a weight to each of the plurality of ranked lists of matches, and
combining the plurality of ranked lists of matches based on the assigned weights to generated the ranked list of genetic diagnoses.

15. The computer-implemented method of claim 1, wherein aggregating the plurality of ranked lists of matches in the output database to generate the ranked list of genetic diagnoses includes executing a learning algorithm based on the data in the mutation proven database and the plurality of dissimilar types of data.

16. The computer-implemented method of claim 1, wherein the ranked list of genetic diagnoses includes a list of causative genes and a gene probability corresponding to each causative gene in the list of causative genes.

17. The computer-implemented method of claim 16, wherein the disease summary includes information indicative of potential implications of the one of the diagnoses at future times.

18. The computer-implemented method of claim 1, further comprising:
receiving, via the network interface, a request for a disease summary corresponding to one of the diagnoses in the ranked list of genetic diagnoses;
generating, by the one or more processors, a disease summary based on at least some of the data in the mutation proven database; and
sending, via the network interface, the disease summary to the end user device.

19. A computer device for automatically diagnosing inherited retinal disease, the computer device comprising:
one or more processors; and
one or more memories coupled to the one or more processors;
wherein the one or more memories include computer executable instructions stored therein that, when executed by the one or more processors, cause the one or more processors to:

receive, via a network interface, a plurality of dissimilar types of data from an end user device, the plurality of dissimilar types of data being related to retinal disease and the plurality of dissimilar types of data corresponding to a patient;

pre-process at least one of the plurality of dissimilar types of data to generate a feature vector descriptive of the patient;

for each of the plurality of dissimilar types of data:

compare portions of the respective type of data or a corresponding feature vector to data in a mutation proven database, wherein the data in the mutation proven database is similar to the respective type of data and wherein the data in the mutation proven database corresponds to a plurality of patients with known diagnoses, generate a ranked list of matches between the patient and the plurality of patients with known diagnoses, and store the ranked list of matches in an output database, aggregate a plurality of ranked lists of matches in the output database to generate a ranked list of genetic diagnoses corresponding to the patient; and send an indication of the ranked list of genetic diagnoses to the end user device.

20. The computer device of claim 19, wherein the plurality of dissimilar types of data includes clinical data and wherein pre-processing at least one of the plurality of dissimilar types of data to generate the feature vector includes:

converting each of a plurality of clinical parameters in the clinical data to a corresponding score, and combining scores corresponding to the plurality of clinical parameters to generate the clinical feature vector representative of the clinical data.

21. The computer-implemented method of claim 1, wherein each of the clinical parameters is individually weighted by a pre-determined function.

* * * * *